United States Patent [19]

Grier et al.

[11] 4,027,009

[45] May 31, 1977

[54] COMPOSITIONS AND METHODS FOR DEPRESSING BLOOD SERUM CHOLESTEROL

[75] Inventors: Nathaniel Grier, Englewood, N.J.; Merwin F. Hoover, Pittsburgh, Pa.; Jesse W. Huff, Westfield; Gunther W. Kuron, Freehold Township, Union County, both of N.J.

[73] Assignee: Merck & Co., Inc., Rahway, N.J.

[22] Filed: Apr. 23, 1974

[21] Appl. No.: 463,071

Related U.S. Application Data

[63] Continuation-in-part of Ser. No. 369,037, June 11, 1973, abandoned.

[52] U.S. Cl. ............................................. 424/78
[51] Int. Cl.$^2$ ...................................... A61K 31/74
[58] Field of Search ................................. 424/78

[56] References Cited

UNITED STATES PATENTS

| | | | |
|---|---|---|---|
| 2,884,057 | 4/1959 | Wilson et al. | 162/164 |
| 3,308,020 | 3/1967 | Wolf et al. | 424/78 |
| 3,383,281 | 5/1968 | Wolf et al. | 424/78 |
| 3,692,895 | 9/1972 | Nelson et al. | 424/78 |
| 3,769,398 | 10/1973 | Hewitt | 424/70 |
| 3,778,476 | 12/1973 | Rembaum et al. | 260/567.6 P |

OTHER PUBLICATIONS

Chemical Abstracts, 68:114988n (1968).

*Primary Examiner*—Leonard Schenkman

[57] ABSTRACT

The invention disclosed herein relates to novel unit dosage compositions comprising 0.1 to 10.0 grams of quaternary poly[(alkylimino)alkylene] linear polymers free from cross-linking, which compositions are valuable as bile acid binding agents; and the invention also relates to the method of binding bile acids by orally administering such compositions.

13 Claims, No Drawings

COMPOSITIONS AND METHODS FOR DEPRESSING BLOOD SERUM CHOLESTEROL

DISCLOSURE OF THE INVENTION

This is a continuation-in-part of U.S. Ser. No. 369,037, filed June 11, 1973, now abandoned.

This invention relates to polymer compositions which are useful for binding bile acids in the gastrointestinal tract of warm-blooded animals. More particularly, this invention relates to the binding of bile acids with polymers having a linear backbone comprising salt-forming nitrogen atoms linked to each other through alkylene groups and which backbone is free from both branching and cross-linking. In particular, this invention relates to methods for lowering blood serum cholesterol levels, as well as relieving symptoms of biliary pruritus.

All available evidence indicates that the incidence of higher than normal blood serum cholesterol levels in humans (especially in so-called Type II Frederickson patients) is associated with atherosclerosis and other hypercholesteremic disease signs. Atherosclerosis is manifested by the effects of occlusion of the circulation, giving rise to coronary, cerebrovascular, and some forms of peripheral vascular disease signs. It is the leading cause of death in many countries, including the U.S. Elevated blood serum cholesterol levels have been the target of various control measures, including restricted and special dietary intake, inhibition of cholesteral synthesis, accelerated catabolism, prevention of gastrointestinal absorption, as well as by means of binding bile acids in the gastrointestinal tract.

It is this latter method with which this invention is especially concerned. The exact means by which bile acid binding in the intestine accomplishes a lowering of blood serum cholesterol levels is unknown; it is believed feedback mechanisms effect cholesterol oxidation responses in an effort to restore bile acid levels. Regardless of the uncertainty of its mechanism the technique is well accepted. What is lacking is a convenient, efficient non-toxic, and easily tolerated binding agent.

Heretofore, a variety of bile acid binding agents have been employed. These include iron salts which produce insoluble precipitates with bile acids, organic bases to act similarly, and polymers having a salt-forming capability. Absorbable precipitants, however, present acute and chronic toxicity hazards. The use of non-absorbable polymers to avoid such toxicity problems has not provided a suitable alternative, because the average effective adult daily dose of such polymers heretofore employed ranges up to 40 grams. The physical bulk of such a dose, especially when of a water-insoluble cross-linked resin, can induce partial blockage of the gastrointestinal tract and an unpleasant, heavy sensation. Furthermore, any objectionable odor and taste of so large a dose is difficult to mask. Gel-type compositions which have less cross-linking, but are branched, as that term is hereafter defined, swell markedly on water sorption, and although relatively free of abrasive irritation, often cause pressure discomfort. Water-soluble polymers heretofore proposed cause very high viscosities in solution, and have marked astringent action in the oral cavity. Furthermore, they present much bulk for consumption, retaining as much as an equal weight of water in dry form. Most seriously they can be degraded in the gastrointestinal tract.

T. M. Parkinson et al, *Atherosclerosis* 11, 531 (1970) reports data illustrating the current state of efficiency of several such agents. This is summarized below in Table I.

TABLE I

| Resin* | Titratable Chloride milliequivalents/ gm. resin | Cholic Acid Binding Capacity | |
|---|---|---|---|
| | | milliequivalents/ gm. resin | gm./gm. resin |
| Tetraethylene pentamine epichlorohydrin beads | 7.5 | 2.0 | 0.82 |
| 2-Diethylaminoethylether of dextran | 4.0 | 2.0 | 0.82 |
| Poly-4-trimethylammoniomethyl styrene chloride crosslinked with 1,4-divinyl benzene | 4.4 | 2.2 | 0.90 |

*base or OH⁻ form

Under in vitro laboratory conditions, none of the resins bind at least their own weight of bill acid. In vivo performance is often reduced by factors of ten or more.

Consequently, there has been only limited benefit derived from treatment by this method, although the incidence of disease linked to hypercholesteremia is extremely high and continues to rise alarmingly.

Several explanations are advanced for the inability of resins heretofore suggested for use as hypercholesterolemics to match bile acid uptake with chloride capture. One view holds that smaller inorganic anions can easily reach binding sites. Therefore, to make a more efficient resin one should provide greater separation of binding sites for bulky acids. Another view holds that resins need to be more lipid-like to penetrate in vivo micelle formations holding fat-like bile acids, thus leading to suggestions that decreased water solubility for resins was desirable.

Unfortunately, these concepts have produced little improvement when translated into polymer design for treating hypercholesterolemia.

We have now found that polymers or resins having a linear polymer backbone which is neither branched nor cross-linked, comprising monomer units of salt forming nitrogen atoms linked to each other through alkylene groups, preferably polymethylene groups, or alternatively through monohydroxy substituted $C_3$ to $C_8$ alkylene groups wherein the hydroxyl group is on a carbon atom other than one linked directly to a nitrogen atom, are exceptionally effective in binding or sequestering bile acids in the gastrointestinal tract, and in lowering blood serum levels of cholesterol.

By the term "salt forming nitrogen" is meant a nitrogen e.g., an imino group or a substituted imino group sufficiently basic that it is either present in the form of a quaternary or an acid addition salt or can form one with acids in the gastrointestinal tract.

The term "linear polymer backbone" is intended to describe a polymer having only acyclic groups linking the nitrogen atoms.

The term "unbranched" is intended to mean a polymer having no repetition of monomer units extending from the polymer backbone and the term "cross-linked" is used in the usual sense to denote a joining of two linear backbones.

Our compounds have the structure:

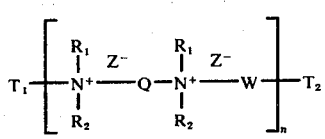

Formula I wherein Q is $(CH_2)_x$ and W is $(CH_2)_y$ and where when x is the integer 2, y is an integer of from 4 to 8 inclusive, and where x is an integer of from 3 to 8 inclusive, y is an integer of from 3 to 8 inclusive; or where Q and W are $C_3$ to $C_8$ hydroxy substituted straight or branched chain alkylene groups wherein the hydroxy substituent is on a carbon atom other than one bonded directly to nitrogen, e.g., (2-hydroxypropylene), 1,4-(3-hydroxybutylene) and the like; $R_1$ and $R_2$ are hydrocarbon radicals, e.g. $C_1$ to $C_4$ alkyl, especially methyl or ethyl; Z is a physiologically acceptable anion less tightly bound than would be an anion from a bile acid, or making a polymer salt more soluble or less stable than bile acid salts, and represents an anion which counters the charge on the quaternized or protonated imino group, and thus can be a monovalent anion. It is to be understood, however, that Z is contemplated to include polyvalent anions where one anion can counter the charge on more than one imino group. Thus, Z can include anions of inorganic acids, as well as from organic acids such as, for example, halide, e.g. chloride, bromide, or iodide; sulfate; bisulfate; phosphate; acetate, ascorbate; carbonate; bicarbonate; nicotinate, methosulfate, salicylate, and other anions derived from physiologically non-toxic acids, especially salts of physiologically active acids such as those derived from the clofibrate and halofenate, i.e., 2-(p-chlorophenoxy)-2-methylpropionic and 3-trifluoromethylphenoxy)-4-(chlorophenyl) acetic acids. When such anions of physiologically active compounds are used to neutralize quaternized or protonated imino groups, it is apparent that only a portion of the imino group may be so neutralized. The amount of anion from the physiologically active compound is apportioned in a ration such that the amount administered with the polymer dosage can fall within the desired range for the physiologically active compound.

$T_1$ and $T_2$ are a suitable terminal group, dependent, as shall be seen on the monomer system employed in preparing the polymer; and n is an integer within a range such that the molecular weight of the resin is greater than 1500.

While it is contemplated that the polymers employed in our invention are most preferably homopolymers, it is satisfactory to employ copolymers where copolymerization is carried out by means well known in the art employing a plurality of monomers described herein to prepare the homopolymers described in Formulas I and II.

In such instances of copolymerization it is readily apparent that the R substituents on adjacent nitrogen atoms in the polymer backbone in Formula I can differ.

In the above structures, $T_1$ is

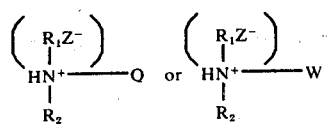

and $T_2$ is

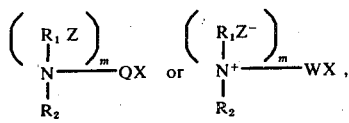

where Q, $R_1$, $R_2$, m, Q and W are as defined, and X is a halogen. Yet it should be noted that the identity of $T_1$ and $T_2$ are not material to the functioning of the resin in this invention. After polymerization, X can be replaced by means known in the art with hydrogen or other suitable non-toxic group.

These polymers are administered orally in an effective bile acid binding dose. For lowering blood serum cholesterol levels, generally a single or multiple dose of from about 0.1 to 5.0 grams is suitable in mammals although doses in excess of 10 grams can be given where indicated. Such doses are also effective in relieving symptoms of biliary pruritus. Administration can be in a variety of forms, such as a suspension, in an aqueous solution, as a chewable or a coated tablet, or in a capsule, and can be continued for an extended course of treatment. Generally, medication is on a daily basis with each day's dose taken in divided portions, preferably with meals.

For control of hypercholesterolemia, the particular individual dosage, given variances in metabolism and diet, is preferably arrived at through an initial determination and continued monitoring of blood serum cholesterol levels. Thus, a moderate dosage might be employed initially, and increased until the desired blood serum cholesterol level is achieved and maintained. For an initial dose, pending such individual adjustment, from 2.5 to 100 mg./kg. of body weight is satisfactory.

Included among the more suitable resins for use in this invention are the linear, unbranched, non-cross-linked, poly-N-alkylalkyleneimine salts such as poly-N-methylethyleneimine hydrohalide and quaternized salts thereof; poly-N,N-dialkylalkyl ammonium salts such as poly-N,N-dimethylethyl ammonium halide; and poly-N,N-dialkyltrimethylene ammonium salts, e.g. poly-N,N-dimethyl-2-hydroxypropylene ammonium halide, wherein the term alkyl is in conformity with those structures defined by Formula I.

Such polymers are prepared by techniques known in the art such as for example, the polymerization of substantially equimolar quantities of N,N,N',N'-tetraalkyl-α,ω-diaminoalkanes and α,ω-dihaloalkane, such as N,N,N',N'-tetramethyl-1,3-diaminopropane and 1,4-dioromobutane; as well as homopolymerization of an N,N-dialkylalkyl halide monomer, such as 1,3-dimethylaminopropyl chloride; and the polymerization occuring where a secondary amine, e.g., dimethylamine is reacted with an epihalohydrin, e.g., epichlorohydrin, under non-cross-linking and non-branch forming conditions.

The charged nitrogen polymers above described are classified as ionenes, a nomenclature devised by A. Rembaum, Macromolecules, 3, 87 (1969) as well as A. Rembaum et al, Macromolecules, 5, 261 (1972). In his system, the compound of the structure:

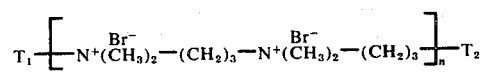

would be referred to as tetramethyl-3,3-ionene bromide. The ionene polymers preferred for use in our invention are the symmetrical ionenes such as tetramethyl and tetraethyl ionene halides and the most preferred tetramethyl-3,3-ionene chloride.

Specifically, the polymers described herein are not to be confused with polymers heretofore suggested for similar uses. Such polymers, although sometimes having a similar name, are replete with cross-linking or branching. While U.S. Pat. No. 3,308,020 teaches the use of $(CH_2CH_2NHCH_2CH_2NH)_n$ for use in lowering blood serum cholesterol, actually, this reference describes a polymer having a high degree of branching. In addition, the tetraethylenepentamine epichlorohydrin beads referred to earlier in Table I are cross-linked polymer.

Therefore, the essence of this invention is that the polymers employed in the methods of this invention have polymer backbones which are linear, free of branching and free of cross-linking, and which backbones have salt forming nitrogen groups therein, each of which is functional in binding bile acids.

The surprisingly high efficiencies found for the linear, unbranched and non-cross-linked resins of our invention as bile acid binding agents are in direct opposition to prior teachings. When the binding sites are brought closely together as in the 3,3-ionene polymers, the greatest weight of bile acid per unit weight or resin is captured. The chloride salt form of these ionenes which has high water solubility appears also to be among the more efficient of the various anionic derivatives. One theory we propose but do not wish to be bound to for explaining the unexpected results is based upon "electronic deshielding". That is, by removing branching and cross-linking, each nitrogen in the polymer backbone is available and functions independently of the anion size. Close spacing linearly of such groups allows for a greatly increased charge density. This combination appears to override obstacles to bile acid micelle penetration, a barrier heretofore considered more accessible to primarily lipid-like agents.

The polymers used in our invention are capable of binding from at least 1.5 to more than 4.5 times their weight of bile acids. There is a direct correlation between the corresponding monomer molecular weight and the stoichiometric equivalent weight uptake of bile acids. Experimental titration tests indicate that every nitrogen group in the polymer backbone forms a salt with one equivalent of bile acid. Our polymers having molecular weights of at least 1500 form non-absorbable bile acid salts with efficiencies in excellent agreement with calculated values. Those polymers with molecular weights above 50,000 perform similarly; stoichiometric salt formation being independent of molecular weights.

Those special techniques which must be employed to prepare polymers or resins free from branching, cross-linking and which are linear will be described.

In general, useful resins can be prepared from AB-type monomers of the structure:

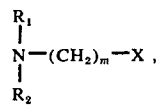

where X is chloro, bromo or iodo, $m$ is an integer 3, 7 or 8, and $R_1$ and $R_2$ are as before, by storage at ambient temperatures, neat or in solutions with such organic solvents as ether, chloroform, methanol, dimethylsulfoxide, dimethylformamide, or in water and water-solvent mixtures. For accelerated polymerization temperatures of up to 125° C. suffice, and to convert particular cyclic intermediates to linear ionene polymers the reaction mixture can be brought to 200° C. as will be described. The processes can be operated in the presence of oxygen (air) for lower molecular weight polymers, those having molecular weights from 1500–10,000 and under nitrogen or in vacuo for higher molecular weight products.

Thus, by this technique there can be prepared tetramethyl and tetraethyl:
 3,3-ionene halide;
 7,7-ionene halide; and
 8,8-ionene halide.

Another method for synthesizing ionenes especially those of varying polymethylene group separation between the charged backbone nitrogen atoms, i.e., unsymmetrical ionenes, requires step growth conditions to avoid branching and cross-linking and yet promote linearity. The process is based on the reaction of alkylenediamines (III) with dihalides of structure IV to provide linear polymers of structure V.

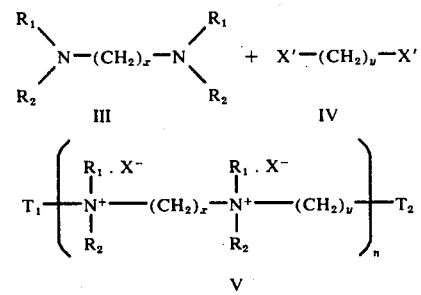

where X, $n$, $T_1$, $T_2$, $x$ and $y$ are as heretofore defined, but $x$ is not, in this instance the same integer as $y$. A 1:1 molar ratio of dihalide and diamine is employed and reaction temperatures are 20°–25° C.

Solvents such as methanol, dimethylformamide, dimethylsulfoxide, tetrahydrofuran, and benzene, or mixtures of these, can be used. Reaction times may vary from several days to several months. Generally, the bromo derivatives are preferred and the resultant polymers precipitate from the reaction mixture. After filtration, addition of a relatively large volume of acetone provides a second precipitated fraction from the liquor. The products are solvent washed and dried under vacuum at 30°–50° C.

By such methods there can be prepared the tetramethyl; traethyl; monomethyltriethyl; diethyldimethyl; and monoethyltrimethyl:
 2,4-ionene halide;
 2,5-ionene halide;
 3,3-ionene halide;
 3,4-ionene halide;
 3,5-ionene halide;
 4,4-ionene halide; and
 4,5-ionene halide.

To prepare symmetrical ionenes, a preferred technique utilizes the intermolecular quaternization of $\alpha,\omega$-haloalkyldialkylamine.

Compounds in the molecular weight range, 1500–6000 and higher are obtained by allowing the bromo derivatives to stand either without solvent or in solvent such as ether or benzene at room temperature for periods of hours to several weeks. Alternately, polymerization can be accomplished by heating neat at 75°–150° C. for at least several hours. Under certain conditions, e.g., in very dilute solution ω-bromopropyldimethylamine will react intramolecularly to form a cyclic quaternary ammonium salt. This monomeric product when heated at 200° C. for a short time converts to a linear polymeric salt, $n$ indicating a molecular weight of about 3600.

ω-Bromopropyldiethylamine on standing at ambient temperature first forms cyclic diethyltrimethyleneammonium bromide, which with additional time in the reaction mixture converts to the linear polymeric quaternary ammonium salt, molecular weight of about 10,000–11,000, unless polymerization is interrupted sooner.

Higher molecular weight ionenes of a weight average molecular weight of at least 50,000 are also prepared from ω-halogenoalkyldialkylamines, but under conditions excluding oxygen, such as in a nitrogen atmosphere. Typically, very concentrated solutions of 3-chloropropyldimethylamine in dimethylsulfoxide or dimethylformamide containing less than 25% by volume of water and under a nitrogen atmosphere are heated at temperatures ranging from 25°–110° C. for from 4 hours to several days. The polymerization may also be run in water, or mixtures with methyl alcohol, in the absence of water as in chloroform or acetonitrile, or for lower molecular weight but linear, non-branched and non-cross linked polymers even in the presence of air.

The process of the polymerization is readily monitored using analysis of ionic halogen, NMR determination of protons on quaternary ammonium groups or visible characteristics such as increased viscosity or polymer precipitation. Generally, unconverted monomer and low molecular weight products are removed by washing with acetone or solvent mixtures. Pure polymer products resulting from substantially complete monomer conversion can be isolated by simply drying the reaction mixture or diluting with acetone, ether, and anhydrous isopropyl alcohol to cause precipitation. The products may then be dried under vacuum at 25°–50° C., powdered and stored in closed containers.

Other variations may be employed in the preparation of these resins as are known in the art, such as the use of catalysts, inert gas atmospheres of hydrogen, helium or argon, polymerization as emulsions or suspensions wherein the growing polymer comprises one phase or is dissolved in one phase and the like. Techniques for monitoring the progress of the polymerization include viscosity measurements, infrared analysis for quaternary ammonium groups, titration of ionizable halogen, NMR determination of alkyl-type protons attached to quaternary ammonium groups, etc. The isolation or purification if required of resultant linear ionene polymers may be by filtration and washing of precipitates, solvent precipitation, dialysis or reverse osmosis membrane filtration and drying by freeze techniques, spraying, vacuum drum or vacuum shelf or simply by evaporation.

Replacement of the halide anion in these polymers with other pharmaceutically acceptable anions may be accomplished by methods well known to the art. For example, dilute polymer solutions can be treated with insoluble ion exchange resins previously converted to the hydroxide form. The hydroxide of the ionene at 25° C. or even lower may then be neutralized with the appropriate acid. An excess of acid may also be present with no deleterious effects on stability. Metathesis offers a second method. Sulfate ionene salts may be reacted with the appropriate calcium or barium salts to produce insoluble calcium or barium sulfate and the ionene salt.

Further specific example will serve to illustrate the preparation of linear, unbranched non-cross-linked polymers.

EXAMPLE I

Polymerization of γ-Chloropropyldimethylamine

High molecular weight 3,3-ionenes are obtained as follows:

Dissolve 72 gms. of 3-dimethylaminopropyl chloride in 28 ml. of water. The solution (5.9 moles/liter) is heated under nitrogen at 100° C. for 50 hours. There is quantitative conversion to the ionene. The product could be isolated by stripping the water off under reduced pressure in a rotary evaporator and drying the residue at 60° C. for 24 hours. Its molecular weight is greater than 20,000.

Alternatively, 24.3 gms. of 3-dimethylaminopropyl chloride in 100 ml. of a solution (2.0 molar) containing dimethylformamide and water (4:1 ratio) heated in the absence of oxygen at 54° C. for 48 hours undergoes an 86% conversion to the 3,3-ionene chloride. Removal of solvents by distillation under reduced pressure, along with unchanged monomer and low boiling by-products, left the product as a semi-solid. An acetone wash, followed by thorough drying under reduced pressure at 40° C., provided a solid which could be pulverized after chilling. Its molecular weight is at least 20,000.

EXAMPLE II

Conversion of Dimethyltrimethyleneammonium Bromide (Dimethylazetidinium bromide) to the 3,3-Ionene Polymer Dimethyltrimethyleneammonium bromide is prepared by allowing a solution of 11.5 g. of gamma-bromopropyldimethylamine in 7 liters of ethyl alcohol to stand 40 hours at room temperature. The solution is concentrated to about 25 ml. under reduced pressure on the steam bath, filtered and mixed with several volumes of anhydrous ether; 10.7 g. precipitated.

A sample (0.08 g.) is heated at 200° C. in an oil bath for 3 minutes. It is suspended in 3 ml. of hot alcohol and enough water added to just cause solution. The solid is precipitated from solution by the addition of an excess, 12 ml. of anhydrous ether. The solid (0.09 g.) melted at 240°–250° C. and is identical to the polymer obtained by the spontaneous condensation of γ-bromopropyldimethylamine, mol. wt. 4980.

On long standing, months, γ-bromopropyldiethylamine forms the homolog, N,N-diethyl-3,3-ionene bromide, m.p. 258°–260° C., mol. wt. 10,800. Heating of the cyclic salt did not convert it to the ionene.

EXAMPLE III

Polymerization of γ-Bromoheptyl, and ω-bromooctyldimethylamines

A variety of conditions are useful for carrying out the polymerization:

γ-Bromoheptyldimethylamine is heated at 75° C. under 3 mm. pressure. A white powder resulted, m.p.

247°–250° C. having a molecular weight of 3400–3800 and 33.6% ionizable bromine.

The same monomer is allowed to stand overnight at room temperature. The white solid polymer obtained has 35% ionic bromine and a molecular weight of 28,000.

ω-Bromooctyldimethylamine is heated at 114°–115° C. under 10 mm. pressure. A thick resinous polymer resulted, mol. wt. 3500 and ionic bromine, 31.55%.

In all runs at least 90% of the total initial bromine is converted to ionic form as a result of ionene formation.

EXAMPLE IV

Polymerization of γ-Bromopropyldimethylamine

The bromoamine is polymerized by heating the pure liquid at steam-bath temperatures; by allowing the solution in ethyl alcohol to stand at room temperature and at 0°–10° C.; and by allowing the solution in anhydrous ether to stand at room temperature. The polymeric material which forms in a very hygroscopic white solid melting at from 225°–240° C. Samples are purified by dissolving the crude material in 90% methyl alcohol and precipitating the polymer with ethyl acetate. The samples are dried at 76° C. over phosphorus pentoxide in high vacuum. Yields of polymer varied from 30–95%, the highest obtained by allowing the neat liquid to stand at room temperature. Ionic bromine analyses ranged from 44–47%. Molecular weights are above 1500.

EXAMPLE V

Preparation of Unsymmetrical Ionene Polymers a. 6,3-Ionene Polymer 0.1 Mole of N,N,N',N'-tetramethyl-α,ω-diaminohexane and 0.1 mole of α,ω-dibromopropane in 65 ml. of (1:1) dimethylformamide-methanol is allowed to stand at 25° C. for 168 hours. Removal of solvents under reduced pressure is followed by a benzene wash of the residue which solubilizes unreacted dibromoalkane and leaves a solid after vacuum drying. Conversion to the ionene polymer is 87% and all of the bromine is ionic, molecular weights are above 10,000.

The same concentrations, solvent mixture and reaction time as in (a) above is used with N,N,N',N'-tetramethyl-α,ω-diaminohexane and α,ω-dibromohexane. The ionene polymer precipitates in 98% yield affording only ionic bromine in good agreement with theoretical values.

The 3,4-ionene polymer required 263 hours for 99% conversion under the same conditions and remained in solution. Isolation is accomplished as described in (a) and all bromine is ionic.

Other unsymmetrical ionenes can be prepared using from 120–263 hours for conversion at 25° C. Yields of at least 50% and up to 100% are realizable. Lower molecular weight fractions can be separated by solubilization, osmometry, gel filtration and other well known techniques.

EXAMPLE VI

Dimethyl-2-Hydroxy-3-Ionene Chloride Polymer

2-Hydroxy-3-dimethylaminopropyl chloride is obtained from the reaction of epichlorohydrin and dimethylamine (10% molar excess) by addition of halohydrin to the amine at 15° C. and after one hour warming the reaction mixture to 20°–25° C. At the end of another hour reaction was complete and excess dimethylamine was stripped at 2–6 mm. pressure.

86.6 Gm. (0.63 mole) of 2-hydroxyl-3-dimethylaminopropyl chloride in 10.0 ml. deionized water is heated under an oxygen-free atmosphere (nitrogen) at 100° C. for 24 hours. After cooling to 20° C. sufficient acetone is added to precipitate the polymer. The isolated product is dried at 50° C. in vacuo to a residual water content of 12.4%. The polymer molecular weight by end group ($CH_3N$—$CH_3$) titration is approximately 4400 and has an intrinsic viscosity in 0.4 MKBr at 30° C., (ω)=0.11 dl/g.

EXAMPLE VII

Preparation of Tetramethyl-3,3-Ionene Ascorbate 6.1 Grams (0.05 moles) of tetramethyl-3,3-ionene chloride is dissolved in 75 ml. of distilled water and passed doewn a column containing 100 gms. (0.5 mole $Cl^-$ exchange capacity) of a polystyrene resin, the benzene ring of which is substituted with 4-methotrimethyl ammonium hydroxide (Bio Rad AG 1 × 8). Two volumes of the eluate (150 ml.) containing tetramethyl-3,3-ionene hydroxide is collected, cooled to 15° C. and neutralized with 8.8 gms. (0.05 moles) of ascorbic acid, U.S.P. The clear neutralized solution is then shell frozen and freeze dried to give a white solid which is readily pulverized.

The other polymers of this invention can likewise be transformed to the ascorbate salt, or by employing other acids containing physiologically acceptable nontoxic anions in place of the ascorbic acid, there can be obtained the other salts heretofore described.

Effective lowering of cholesterol blood vessels is obtained by the oral administration of remarkably small dosages of the polymers of this invention. This enables a flexibility of formulation previously unavailable. The polymers can be finely divided powders and suitably used as such or preferably admixed with varying amounts of solid carrier agents such as collodial silica, starches, sucrose, talc, lactose, cellulose, or modified cellulose, dry milk powder, protein powders such as soy flour, and the like. These are preferably made into unit dosage forms such as tablets, filled gelatin capsules, or a foil or paper envelope containing the premeasured dose which can include supplementary vitamins and minerals, and which can be readily torn open and added to edible liquids such as fruit juices or other beverages. The unit dose composition may comprise from 10% to 99% by weight of polymer, the remainder being carriers, flavorings, excipients, flow agents and the like. In such a unit dose, the active polymer may comprise from 0.1 gm. to up to 10 gms. in powder packets.

Also suitable are aqueous solutions or suspensions which can be prepared and are preferably sweetened or flavored. Although not entirely desirable, the polymers can be mixed in various vehicles such as safflower or corn oil for oral ingestion as such or as an aqueous emulsion. These may also be encapsulated.

As hereinbefore stated the total daily dosage of bile acid binding polymer is preferably divided into portions and taken before each meal and prior to bedtime. This regimen provides for maximum resin contact time during periods of highest intestinal bile acid concentrations.

The polymers of this invention may be used alone, or, if desired, can be compounded together with triglyceride synthesis inhibitors or other bile acid binding agents for particular treatments. In addition, the polymers described herein form salts with chlorofibrate and halofenate, which salts are useful in cardiovascular diesase therapy. When so used, the polymer salt of chlorofibrate or halophenate can be combined in admixture with other salts of the linear polymer to achieve the desired balance of dosage. The following examples are illustrative of the dosage forms which can be employed in the practice of our invention. Those skilled in the art of pharmaceutical compounding will be aware of variations which can be practical without departing from the spirit of our invention. It is anticipated that multiple dosages, e.g., two or three tablets or capsules can be taken at one time if higher dosages are prescribed.

Additional ingredients which may comprise the carrier portion of the compositions of this invention, can also have pharmacological activity and can include other choleretic agents such as tocamphyl floranty-rone; taurine; and glycine; hypocholesteremic agents such as nicotinic acid; the D-isomer of 3,3',5-triiodothyronine; thyroxine-like compounds such as sodium L-thyroxin and sodium D-thyroxine; triiodothyropropionic acid; nafoxidine hydrochloride, 5-methylpyrazole-3-carboxylic acid and 3-methyl-5-isoxazolecarboxylic acid; fecal softeners such as poloxalkol and dioctyl sodium sulfosuccinate; as well as unsaturated fatty acids such as linoleic acid, arachiodonic acid and linolenic acid; edible vegetable oils such as corn oil and safflower oil.

POWDER PACKETS

Linear, unbranched and non-cross-linked poly-(N,N-dimethyltrimethylene-ammonium chloride) molecular weight 50,000 is finely powdered and blended with 1% by weight of lactose powder. Aluminum envelopes containing a paper bag liner are individually filled with 0.55 g. of the mixture and sealed against moisture to prevent caking.

In place of the 3,3-ionene polymer chloride there can be substituted the 2,2-homolog or other polymers described herein, having various molecular weights from 1500 to 70,000 and comprising polymers of a single average molecular weight or mixtures of varying molecular weights, so long as in excess of 1500.

HARD GELATIN CAPSULES

The same dosage, i.e., 0.55 g., of poly-(N,N-dimethyltrimethylene-3-ammonium chloride) containing 1% by weight of lactose as described above is filled into the appropriate size hard gelatin capsules.

Alternatively, a dry filled capsule can be prepared from the following components:

| | |
|---|---|
| 2,4-ionene chloride | 300 mg. |
| corn starch | 150 mg. |
| Cab-o-sil (anhydrous silica) | 5 mg. |

Dry filled capsules can likewise be prepared using 2,6-ionene chloride, 3,4-ionene bromide, 2,4-ionene and any other of the compounds set forth in this specification. If capsules of lower potency are to be prepared, the capsule size can be decreased or additional corn starch or other diluent employed. When using smaller amounts of active ingredient it is anticipated that a multiple capsule dose can be administered.

COMPRESSED TABLETS

A dry blend is prepared with the following components:

| | |
|---|---|
| poly-(N,N-dimethyltrimethylene-3-ammonium chloride) | 1 kg. |
| sucrose, powdered | 30 gms. |
| colloidal silica | 10 gms. |
| carbowax 4000 | 30 gms. |

Four thousand tablets are pressed therefrom by direct compression each of which tablets contains 250 mg. of the ionene polymer.

Likewise, compressed tablets are prepared such that each tablet contains:

| | |
|---|---|
| 4,3-ionene chloride | 300 mg. |
| corn starch | 30 mg. |
| polyvinylpyrrolidone | 10 mg. |
| magnesium stearate | 3 mg. |

After tableting, a plastic film can be applied to the tablets to seal them from moisture in ways well known in the art.

In addition, an enteric coating may be applied if desired. Such a coating may comprise fats, fatty acids, waxes and mixtures thereof, shellac, ammoniated shellac, and cellulose acid phthalates applied by techniques well known and accepted.

In place of the tetramethyl-3,3-ionene chloride polymer there may be substituted any of the polymers of our invention.

Other binding agents may be used in place of sucrose, such as dextrose, lactose, methyl cellulose, natural and synthetic gums, and the like. Talc can replace the calcium or magnesium stearate. A variety of readily available non-toxic anti-caking agents may be substituted for the colloidal silica.

Other lubricants, diluents, binders, coloring agents, flavoring agents and disintegrators can be used as are known in the art employing wet or dry granulation techniques, direct compression, spray drying and the like.

If desired, a chewable tablet can be prepared from preferably microencapsulated polymer particles by dry granulation as follows:

| | In Each Tablet |
|---|---|
| Microencapsulated 3,3-ionene chloride | 750 mg. |
| Mannitol | 300 mg. |
| Sodium Saccharine (or other artificial sweetener) | 2 mg. |
| Oil of Peppermint | 1 mg. |
| Carbowax 4000 | 10 mg. |
| Microcrystalline Cellulose | 100 mg. |

To illustrate the serum cholesterol lowering properties of the resins herein disclosed six Beagle dogs (average weight — 11.4 kg.) maintained in individual cages were administered a semi-purified diet once daily and plasma cholesterol values determined semi-weekly until a plateau level was reached. For the "control-period" data, six semi-weekly values were then obtained over the next three weeks and averaged. Each dog was then given 1.2 gm. of 3,3-ionene chloride, molecular weight 50,000 to 70,000 per day by mixing it into the daily ration of food. Plasma cholesterol levels were determined semi-weekly until they had stabilized at the new levels (usually 2 weeks). For the "treatment-period" data, six consecutive semi-weekly values were then obtained over the next three weeks and averaged. The plasma prepared from heparinized blood was analyzed for cholesterol by the method of Abel et al (J. Biol. Chem., 195:357, 1957). Results are expressed as mg. of cholesterol per 100 ml. plasma (i.e., mg.-%). The diet employed had the following composition: purified casein — 33.50%, dextrose — 45.15%, bone ash — 2.85%, lard — 13.00%, cod liver oil — 2.5%, cellulfour — 5.15%, salt-mixture — 3.00%, and vitamin supplement. The following data were obtained:

| Dog Number | Plasma Cholesterol | | % Reduction |
|---|---|---|---|
| | Control Period[1] (mg.-%) | Treatment Period[1] (mg.-%) | |
| 1 | 188.0 | 92.0 | 51.1 |
| 2 | 161.0 | 127.3 | 21.1 |
| 3 | 176.1 | 112.2 | 36.3 |
| 4 | 155.2 | 122.7 | 20.9 |
| 5 | 141.0 | 96.3 | 31.7 |
| 6 | 152.0 | 121.7 | 19.9 |

[1]Each value represents the average obtained during a period of at least six semi-weekly bleedings.

To generally illustrate the efficiency as a sequestrant of bile acids, compounds disclosed herein were equilibrated for 15 minutes with an aqueous bile acid solution of sodium taurocholate (Nutritional Biochemicals Corporation, Cleveland, Ohio). Subsequently, the mixture is filtered, acidified, and extracted with a suitable solvent. The bile acid content of the extract, representing unabsorbed bile acids is determined spectrophotometrically (Erickson, S. and J. Sjorall, ARKIV. KEMI 8: 311, (1955). Uptake capacity is expressed as g. taurocholate per g. of polymer. The following data were obtained with this procedure:

| Polymer | Uptake Laurocholate/g. of Polymer |
|---|---|
| 3,3-Ionene Cl | 4.70 |
| Polyethyleneimine HCl (linear, unbranched) | 14.3* |
| 2-Hydroxy-3,3-Ionene Chloride | 3.1 |

*Calculated as the free base

What is claimed is:
1. A method for lowering mammalian blood serum cholesterol levels and binding bile acids in the gastrointestinal tract comprising orally administering an effective bile acid binding dose of a polymer having linear backbone which is neither branched nor crosslinked of the structure:

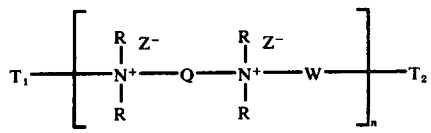

wherein Q is $(CH_2)_x$ and W is $(CH_2)_y$ and, when $x$ is the integer 2, $y$ is an integer of from 4 to 8 inclusive, and when $x$ is an integer of from 3 to 8 inclusive, $y$ is an integer of from 3 to 8 inclusive; or Q and W are $C_3$ to $C_8$ hydroxy substituted straight or branched chain alkylene groups wherein the hydroxy substituent is on a carbon atom other than one bonded directly to nitrogen; R is $C_1$ to $C_4$ alkyl; Z is a physiologically acceptable anion; $T_1$ and $T_2$ are terminal groups, and $n$ is an integer within a range such that molecular weight of the polymer is 1,500 to 70,000.

2. A method according to claim 1 where said physiologically acceptable anion 2 is chloride, bromide, iodide, carbonate, acetate, ascorbate, palmitate, stearate, benzoate, nicotinate, salicylate or hydroxycitrate.

3. A method according to claim 1 in which each R is methyl and Q is $(CH_2)_x$ and W is $(CH_2)_y$.

4. A method according to claim 1 in which Z is halide.

5. A method according to claim 1 in which Z is ascorbate.

6. A method according to claim 3 in which $x$ is 3, $y$ is 3, and Z is chloride.

7. A composition for binding bile acid in the gastrointestinal tract of mammals comprising in unit does form from 0.1 to 10.0 grams of a polymer having linear backbone which is neither branched nor crosslinked of the structure:

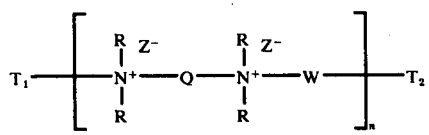

wherein Q is $(CH_2)_x$ and W is $(CH_2)_y$ and, when $x$ is the integer 2, $y$ is an integer of from 4 to 8 inclusive, and when $x$ is an integer of from 3 to 8 inclusive, $y$ is an integer of from 3 to 8 inclusive; or Q and W are $C_3$ to $C_8$ hydroxy substituted straight or branched chain alkylene groups wherein the hydroxy substituent is on a carbon atom other than one bonded directly to nitrogen; R is $C_1$ to $C_4$ alkyl; Z is a physiologically acceptable anion; $T_1$ and $T_2$ are terminal groups; and $n$ is an integer within a range such that molecular weight of the polymer is 1,500 to 70,000, and a said non-toxic physiologically acceptable pharmaceutical carrier.

8. A composition according to claim 7 in which each R is methyl and Q is $(CH_2)_x$ and W is $(CH_2)_y$.

9. A composition according to claim 7 in which Z is halide.

10. A composition according to claim 7 in which each R is methyl, Q is $(CH_2)_x$, W is $(CH_2)_y$, X is 3, Y is 3, and each Z is chloride.

11. A composition according to claim 8 wherein Z is 3-trifluoromethylphenoxy-(4-chlorophenyl)acetate.

12. A composition according to claim 8 wherein Z is 2-(p-chlorophenoxy)-2-methylpropionate.

13. A composition according to claim 8 wherein Z is ascorbate.

* * * * *